United States Patent [19]

Bristol et al.

[11] 4,428,962

[45] Jan. 31, 1984

[54] INDOLES IN TREATMENT OF PEPTIC ULCERS

[75] Inventors: James A. Bristol, Ann Arbor, Mich.; Chester Puchalski, Dover, N.J.

[73] Assignee: Schering Corporation, Kenilworth, N.Y.

[21] Appl. No.: 316,462

[22] Filed: Oct. 30, 1981

[51] Int. Cl.$^3$ ............... C07D 209/42; C07D 209/08; A61K 31/40

[52] U.S. Cl. .................................. 424/274; 548/469; 548/483; 548/505

[58] Field of Search ............ 260/326.11 R, 326.12 R, 260/326.13 R, 326.13 H; 548/469, 483, 505; 424/274

[56] References Cited

U.S. PATENT DOCUMENTS

| | | | |
|---|---|---|---|
| 3,072,530 | 1/1963 | Hofmann et al. | 260/326.12 R |
| 3,076,814 | 2/1963 | Speeter et al. | 260/326.13 R |
| 3,297,717 | 1/1967 | Gould et al. | 260/326.12 R |
| 4,021,448 | 5/1977 | Bell | 260/326.13 R |
| 4,285,962 | 8/1981 | Franzone | 424/274 |

FOREIGN PATENT DOCUMENTS

| | | | |
|---|---|---|---|
| 2727829 | 1/1978 | Fed. Rep. of Germany | 424/274 |
| 2035310 | 10/1978 | United Kingdom | 424/274 |

OTHER PUBLICATIONS

Ek et al., "Synthesis . . . Hydroxy Tryptophan Metabolites, "*A.C.S.* 76:5579–5588 (1954).
Bridges et al. "Fluorescence of Indoles . . . ", *Biochem. J.* 107: 225–237. (1968).
Sarett et al., ". . . Indometacin–Analoge", *Die Entzundung,* Urban & Schwartzenberg, Berlin (1966).
Heacock et al. "Hydroxyskatoles . . . " Chem Abst. 60: 9228d, (1964).

*Primary Examiner*—Donald G. Daus
*Assistant Examiner*—G. H. Hendricks
*Attorney, Agent, or Firm*—Gerald S. Rosen; Bruce M. Eisen

[57] ABSTRACT

There are disclosed herein certain indole derivatives which are useful in the treatment of peptic ulcer diseases.

33 Claims, No Drawings

INDOLES IN TREATMENT OF PEPTIC ULCERS

SUMMARY OF THE INVENTION

This invention relates to certain substituted indole compounds, pharmaceutical compositions thereof, novel processes and intermediates for making said compounds, and methods of treating peptic ulcer disease utilizing said compounds.

More particularly, this invention relates to indole compounds represented by the structural formula:

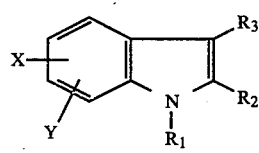

and pharmaceutically acceptable salts thereof, wherein $R_1$ represents hydrogen, lower alkyl of 1–3 carbons or arylalkyl; $R_2$ and $R_3$ each independently represents hydrogen, lower alkyl of 1–3 carbons, —CH$_2$OH, —CH$_2$CN,

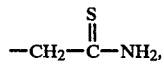

—N(R$_1$)$_2$, —NO$_2$, —NO, —CH$_2$—O—CO—R (wherein R is lower alkyl of 1–5 carbons or dimethylaminomethyl), —S(O)$_n$—CH$_3$, or —CH$_2$—S(O)$_n$—CH$_3$, wherein n is zero, one or two; X represents hydrogen, lower alkyl, halogen, hydroxy, lower alkoxy, or trifluoromethyl; and Y represents —OR$_4$, —NHR$_4$, R$_4$ or —S(O)$_n$R$_4$, wherein n is zero, one or two, and R$_4$ is -lower alkylene-allyl, -lower alkylene-Ar, -lower alkene-Ar, -lower alkene-lower alkylene-Ar or -lower alkylene-O-Ar, in which Ar is substituted phenyl, phenyl, thienyl or pyridyl wherein one or more of the substituents on the phenyl is independently selected from —H, —Cl, —F, —CH$_3$, -t-butyl, —CF$_3$, —OCH$_3$ and —OH; provided that when R$_4$ is lower alkylene-O-Ar, Y is not —OR$_4$, —NHR$_4$, or —S(O)$_n$R$_4$ and when —OR$_4$ is phenylmethoxy, (a) at least one of X, R$_1$, R$_2$ and R$_3$ is not hydrogen, (b) when X, R$_1$ and R$_2$ are hydrogen, R$_3$ is other than —CH$_2$CN or methyl and (c) one of R$_2$ and R$_3$ is other than methyl when phenylmethoxy is in the 4-position.

The preferred compounds of Formula I are those in which Y is in position 7 and R$_1$ represents hydrogen or methyl; R$_2$ and R$_3$ independently represent —H, —CH$_3$, —CH$_2$OH, —CH$_2$CN, —CH$_2$OCOCH$_3$,

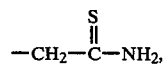

—NH$_2$ or —NO;

X represents hydrogen; and

Y represents —OR$_4$, —NHR$_4$ or —R$_4$ wherein R$_4$ is —CH$_2$—Ar, —CH$_2$—CH$_2$—Ar,

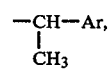

—CH$_2$—CH$_2$—CH$_2$—Ar, —CH=CHCH$_2$Ar or —CH$_2$—O—Ar, wherein Ar is phenyl, o- or p-fluorophenyl, p-chlorophenyl, 2,4,6-trimethylphenyl, 2-thienyl; or 3-thienyl, provided when R$_4$ is —CH$_2$—O—Ar, Y is not —OR$_4$ or —NHR$_4$ and when —OR$_4$ is phenylmethoxy, at least one of X, R$_1$, R$_2$ and R$_3$ is other than hydrogen.

Thus, the preferred Y substituents of Formula I include phenylmethoxy, phenylmethanamino, thienylmethoxy, thienylmethanamino, phenylethyl, phenylpropyl, thienylethyl, thienylpropyl, 3-phenyl-1-propenyl or phenoxymethyl.

The most preferred compounds of this invention are represented by the formula:

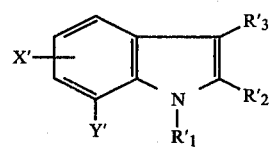

and pharmaceutically acceptable salts thereof, wherein R'$_1$, is hydrogen or methyl;

R'$_2$ is methyl and R'$_3$ is methyl, cyanomethyl or amino;

X' is hydrogen; and

Y' is phenylmethoxy, 2-phenylethyl, or 3-phenyl-1-propenyl.

As used herein "halogen" means fluorine, chlorine, bromine and iodine with chlorine and fluorine preferred. The term "lower" as it modifies radicals such as alkyl, alkylene, alkene and the like, unless otherwise stated, means straight and branched-chain radicals having up to six carbon atoms, e.g. methyl, ethyl, propyl, butyl, t-butyl, isopropyl, neopentyl, dimethylbutyl and the like. Methyl is the preferred lower alkyl.

"Pyridyl" includes the 2-, 3-, and 4- isomers and their halogen and lower alkyl substituted analogs; "thienyl" includes the 2-, and 3- isomers and their halogen and lower alkyl substituted analogs. The substituents on the "substituted-phenyl" radical may be in the ortho, meta and/or para positions, the preferred substituent is halogen. In those compounds in which X is other than hydrogen, it may be at any of the 4,5,6, or 7 positions not already substituted by the Y substituent. "Pharmaceutically acceptable salts" include salts formed by the reaction of the compounds represented by Formula I with pharmaceutically acceptable acids using conventional means. Such acids can be organic or inorganic, e.g. hydrochloric, sulfuric, phosphoric, nitric, acetic, propionic, maleic, ascorbic, citric, and the like.

Examples of indole compounds within the scope of this invention are:
1. 1,2,3-trimethyl-7-phenylmethoxyindole;
2. 2,3-dimethyl-7-phenylmethoxyindole;
3. 2,3-dimethyl-7-(3-thienylmethoxy)indole;
4. 2,3-dimethyl-7-(2-phenylethyl)indole;
5. 2,3-dimethyl-7-(3-phenyl-1-propenyl)indole;
6. 2-methyl-3-cyanomethyl-7-phenylmethoxyindole;
7. 2-methyl-3-amino-7-phenylmethoxyindole;
8. 2-methyl-3-cyanomethyl-7-(2-phenylethyl)indole;
9. 2-methyl-3-amino-7-(2-phenylethyl)indole;
10. 2-methyl-3-cyanomethyl-7-(3-phenyl-1-propenyl)indole;
11. 2-methyl-3-amino-7-(3-phenyl-1-propenyl)indole;
12. 2-methyl-3-amino-7-(3-thienylethyl)indole;
13. 2-methyl-3-amino-7-(3-thienylmethoxy)indole;

14. 2-methyl-3-cyanomethyl-7-(3-thienylmethoxy)indole;
15. 2-methyl-3-amino-7-(2-fluorophenylmethoxy)indole;
16. 2-methyl-3-thiocarbamoylmethyl-7-phenylmethoxyindole; and
17. 2-methyl-3-thiocarbamoylmethyl-7-(3-thienylmethoxy)indole.

DETAILED DESCRIPTION

The compounds of this invention can be prepared by various and alternative methods, depending upon the desired products. The Fischer indole synthesis, Robinson, Chem. Rev., 69, 229 (1969) is used in most cases.

The specific desired substituted aniline starting materials are either known compounds or can be obtained using established procedures to introduce the desired substituents into a benzene ring.

The appropriately substituted phenylhydrazine may be prepared from the corresponding substituted aniline according to the following reaction sequence.

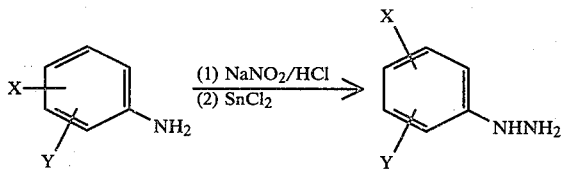

Generally the reaction involves diazotization of aniline with sodium nitrite in hydrochloric acid solution in the cold at about −5° C. to 5° C. followed by reduction either with stannous chloride at a low temperatures or reduction with sodium sulfite in a warm solution of about 60°–70° C.

Introduction of the desired 2- and 3- indole substituents is accomplished by reacting the hydrazine with an appropriate carbonyl-containing compound, e.g. a ketone or aldehyde, in glacial acetic acid or other appropriate solvent at or below room temperature to form the corresponding hydrazone. Heating the hydrazone under reflux in ethanolic hydrogen chloride gives the corresponding indole as shown in reaction Scheme 1.

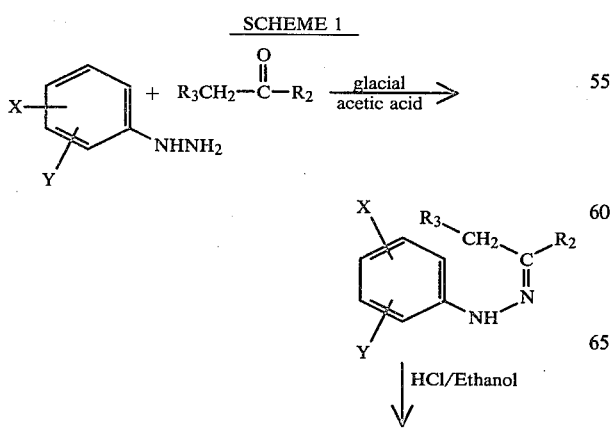

-continued
SCHEME 1

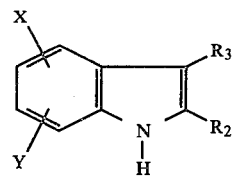

The reaction can also be carried out in one step by heating under reflux the carbonyl compound and the hydrazine hydrochloride in a suitable solvent, e.g. acetic acid, Dave, Org. Prep. Proc. Int. 8 41 (1976).

The Fischer indole synthesis, ibid, can, for example, be used for the preparation of 2- and 3- substituted indoles, such as 2,3-dimethyl-7-phenylmethoxyindole and 2-methyl-3-cyanomethyl-7-phenylmethoxyindole, as shown in reaction Scheme 2. In this case, the appropriately substituted phenylhydrazine starting material is prepared by decomposition of the sydone as described by Smissman, et al., J. Org. Chem. 37,1704 (1972).

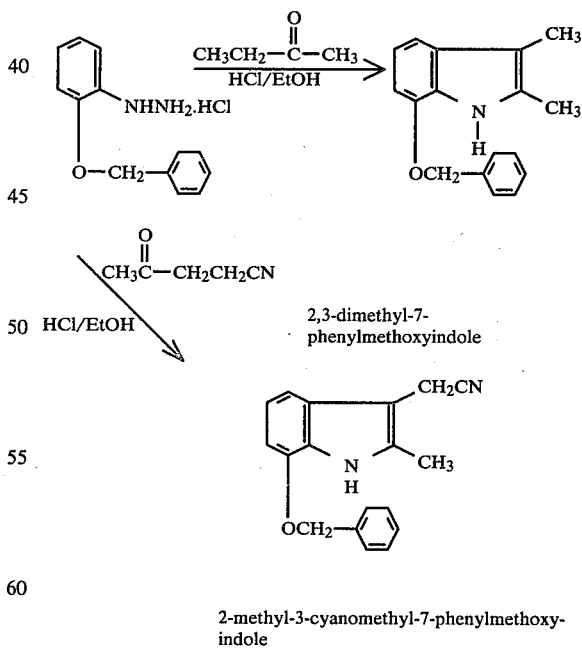

2-methyl-3-cyanomethyl-7-phenylmethoxyindole

Alternative processes for introducing 3-substituents in the indole nucleus are shown in the following reaction Schemes 3 and 4.

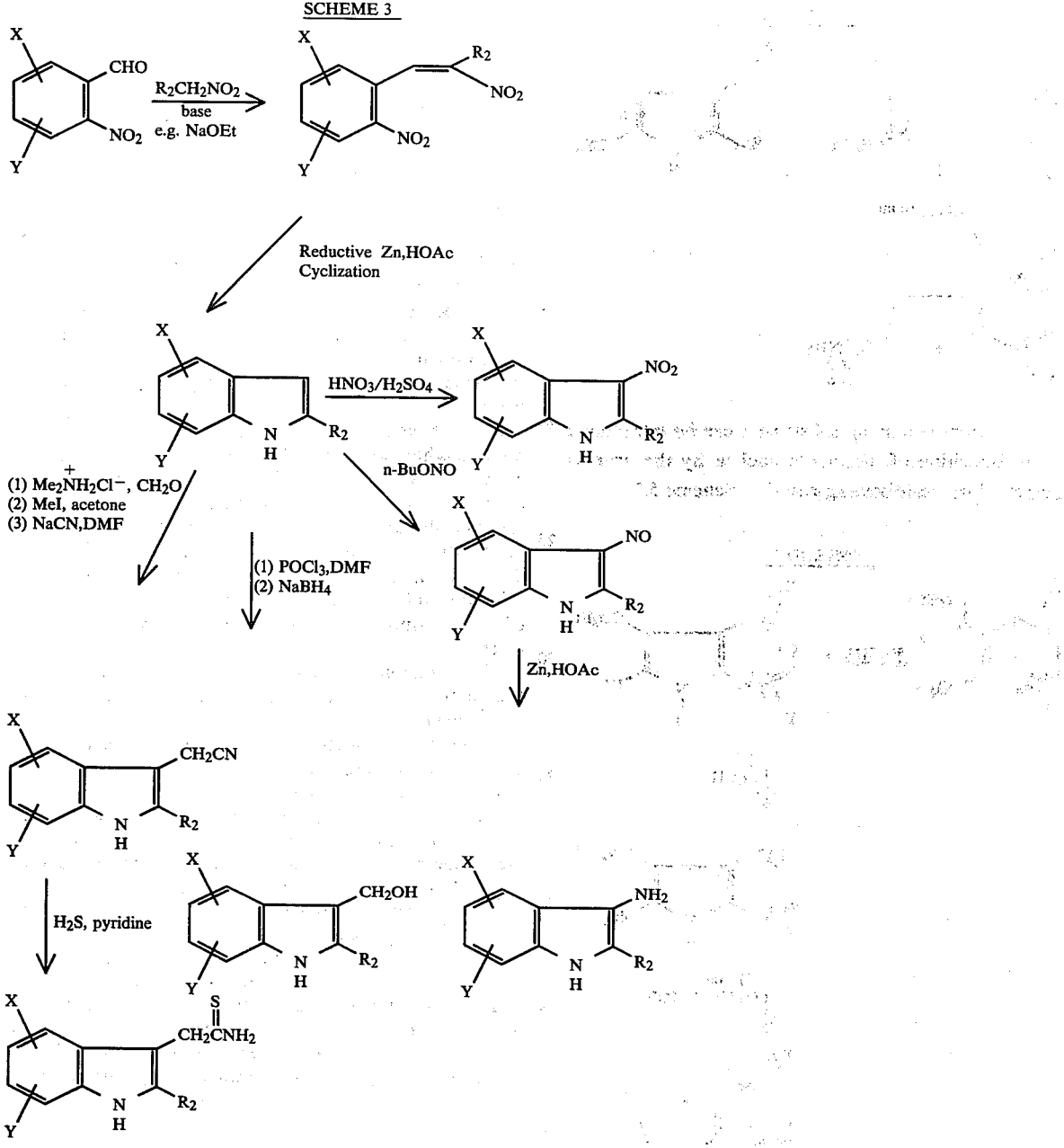
The following reaction Scheme 4 is a modification of the Japp-Klingmann reaction, Phillips. Org. Reactions 10 143 (1959).
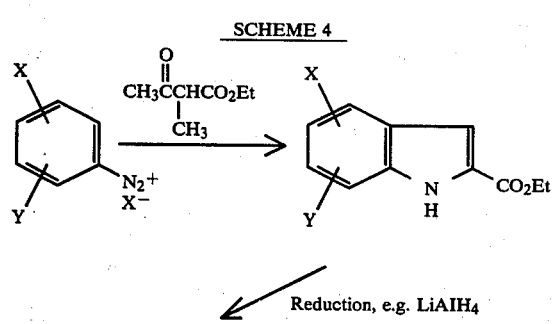
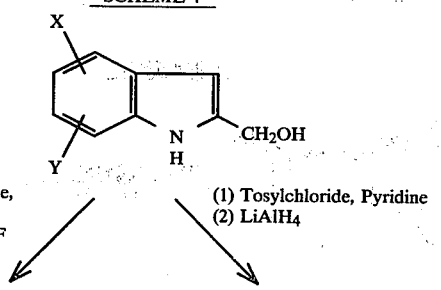

-continued
SCHEME 4

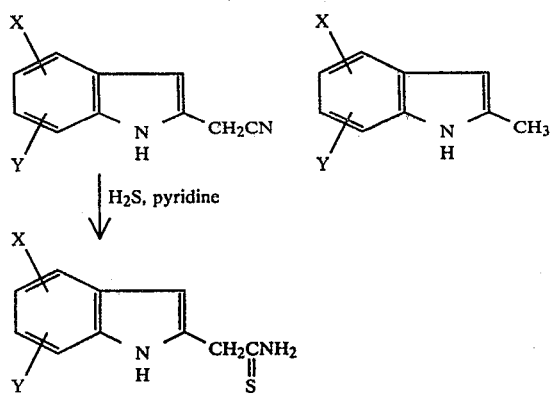

A nitrogen-containing substituent can be introduced at the 2-position of the indole nucleus by the process illustrated in the following reaction Scheme 5.

SCHEME 5

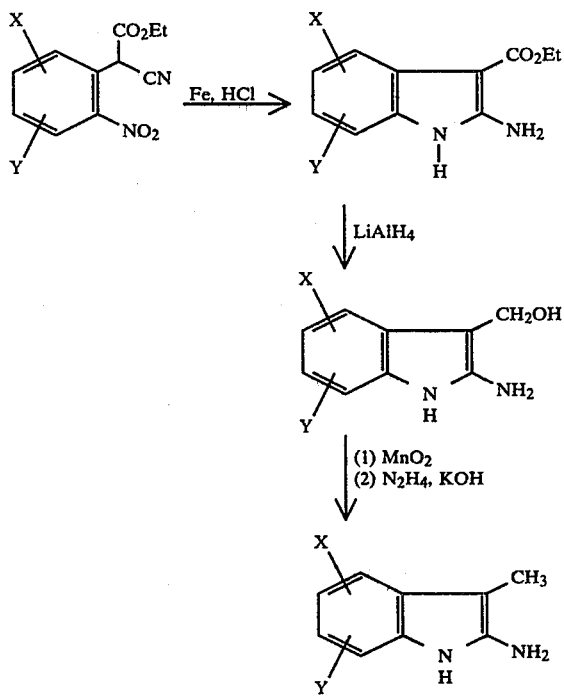

An alkyl group can be introduced onto the nitrogen of the indole according to the following reaction Scheme 6.

SCHEME 6

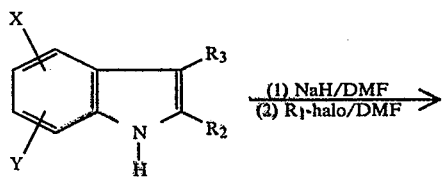

-continued
SCHEME 6

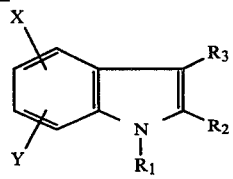

The first reaction takes place in an organic solvent such as dimethylformamide at about room temperature and the second reaction takes place in the same reaction medium in the cold at about $-5°$ C. to $+5°$ C.

The indole compounds of this invention are useful in the treatment of peptic ulcers, have characteristics which enable them to relieve the symptoms of peptic ulcer disease, including stress ulceration, and promote healing of gastric and/or duodenal ulcers. The antiulcer activity of the compounds of this invention is identified by tests which measure their cytoprotective effect (also referred to as mucoprotective effect) and antisecretory effect in rats. The compounds are also useful as conjunctive therapeutic agents for coadministration with such anti-inflammatory/analgesic agents as aspirin, indomethacin, phenylbutazones, ibuprofen, naproxen, tolmetin and other agents having the untoward side effect of contributing damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease and drug induced gastric ulceration. Such tests include testing for antisecretory effects in rats with pyloric ligation techniques. The test compounds are administered in appropriate and well-defined and well-known vehicles either intraperitoneally or orally.

In cytoprotective tests in rats in which ethanol is employed to induce gastrointestinal damage, the compounds of this invention are found to be effective for the oral treatment of the ulcerative disease states mentioned herein at doses of about 0.5–50 mg per kilogram of body weight per day, preferably the total dosages are administered in 2–4 divided doses per day.

When administering parenterally, e.g. intravenously, the compounds are administered at a dosage range of about 0.01 to 10 mg/kg. body weight in single or multiple daily doses. Of course, the dose will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably 600 to 800 mg/day, in two to four divided doses. This dosage regimen achieves relief of the symptoms of peptic ulcer disease and promotes the healing of gastric and/or duodenal ulcers.

To treat peptic ulcer disease, gastric and duodenal ulcers and prevent and treat drug-incuded gastric ulceration, the active compounds of this invention can be administered in unit dosage forms such as tablets, capsules, pills, powders, granules, sterile parenteral solutions or suspensions, suppositories and the like. Such dosage forms are prepared according to standard techniques well known in the art.

The following examples illustrate the preparation of compounds and compositions of this invention. All temperatures are in degrees Celsius.

EXAMPLE 1

A suspension of 8.7 grams o-phenylmethoxyphenylhydrazine hydrochloride and 4.1 grams sodium acetate in 100 ml 2-butanone containing 10 ml glacial acetic acid was stirred at room temperature for 19 hours. The resulting mixture was filtered and the filtrate was concentrated under reduced pressure to yield an oily hydrazone. A solution of the hydrazone in 100 ml ethanolic hydrogen chloride (2.2 M) was heated under reflux for 30 minutes. The reaction mixture was cooled to room temperature, 100 ml water was added and the pH of the reaction mixture was adjusted to pH 12–13 with 25% aqueous sodium hydroxide.

The ethanol was removed under reduced pressure and the basic aqueous layer was extracted with dichloromethane. All extracts were combined and dried over anhydrous sodium sulfate. The dried extracts were filtered and the dichloromethane was removed under reduced pressure. The residue which was obtained was chromatographed on silica gel using 1% ethyl acetate in hexanes to yield a waxy solid, 2,3-dimethyl-7-phenylmethoxyindole as determined by IR, NMR and elemental analysis.

EXAMPLE 2

A suspension of 0.8 gram, 2,3-dimethyl-7-phenylmethoxy indole and 0.24 grams sodium hydride (50% in mineral oil) in 12 ml dimethylformamide was stirred at room temperature for 30 minutes. The reaction mixture was then cooled to 0° and 0.57 gram methyl iodide in 2 ml dimethylformamide was added dropwise with stirring over five minutes. After the addition was complete, stirring was continued at 0° for an additional 1.75 hours. 100 ml water was added and the reaction mixture was extracted with ether. The extracts were combined and dried over anhydrous sodium sulfate. The dried extracts were filtered and the ether removed under reduced pressures. The resulting residue was chromatographed on silica gel, using 2% ethyl acetate in hexanes to yield the product determined by IR, NMR and elemental analysis to be 1,2,3-trimethyl-7-phenylmethoxyindole, m.p. 72°–78°.

The following formulations exemplify some of the dosage forms in which the compounds of this invention may be employed. In each, the active ingredient is designated by the term "Drug" which is meant to indicate one of the following compounds:
1,2,3-trimethyl-7-phenylmethoxyindole and
2,3-dimethyl-7-phenylmethoxyindole.

It is contemplated, however, that each of these exemplar compounds may be replaced by equally effective quantities of other compounds within the scope of Formula I.

Formulation 1

| No. | Ingredient | mg/tab | mg/tab |
|---|---|---|---|
| 1 | Drug | 25.0 | 400.0 |
| 2 | Lactose impalpable powder USP | 114.0 | 241.5 |
| 3 | Corn starch USP | 25.0 | 50.0 |

Formulation 1-continued

| No. | Ingredient | mg/tab | mg/tab |
|---|---|---|---|
| 4 | Corn starch as 5% paste in distilled water | 10.0 | 35.0 |
| 5 | Corn starch USP | 25.0 | 50.0 |
| 6 | Magnesium Stearate USP | 1.0 | 3.5 |
|  |  | 200.0 | 780.0 |

Method of Manufacture

Mix item nos. 1, 2 and 3 in a suitable blender for 5 to 15 minutes. Pass through a fine screen (#40) if necessary. Reblend for 5 to 10 minutes and granulate with item no. 4. Pass the damp granulated mass through a coarse sieve (#6) using a suitable mill. Dry the damp granules at 40° to 50° C. overnight. Mill the dried granules using no. 20 screen. Add item no. 5 and blend for 5 to 10 minutes. Add item no. 6 and blend further for 3 to 5 minutes. Compress the mixture into tablets of an appropriate size and weight using a suitable tabletting machine.

Formulation 2

| No. | Ingredient | mg/tab | mg/tab |
|---|---|---|---|
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium stearate USP | 1.0 | 3.5 |
|  |  | 200.0 | 700.0 |

Method of Manufacture

Mix item nos. 1, 2 and 3 in a suitable blender for 5 to 10 minutes. Pass through a fine screen (#40) if necessary. Reblend for 5 to 10 minutes, add item no. 4 and mix further for 3 to 50 minutes. Using a suitable machine, encapsulate the mixture into a two piece hard gelatin capsule of appropriate size.

Formulation 3

| Ingredients | Formula A (mg/ml) | Formula B (mg/ml) |
|---|---|---|
| Drug | 5.0 | 80.0 |
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.

7. This suspension is then q.s. to final volume with purified water at 25° C.

Formulation 4

| Parenteral | |
|---|---|
| | mg/ml |
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method of Manufacture

1. Dissolve parabens in a portion (approximately 85% of the final volume) of the water for injection at 65°–70° C.
2. Cool to 25°–30° C. Charge and dissolve sodium bisulfite, disodium edetate and sodium sulfate.
3. Charge and dissolve the Drug.
4. Bring the solution to the final volume by adding water for injection.
5. Filter the solution through 0.22 micron membrane and fill into appropriate containers.
6. Terminally sterilize the units by autoclaving.

Formulation 5

| Injectable Suspension | |
|---|---|
| | mg/ml |
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 |

Method of Preparation

1. Dissolve parabens in a portion of water for injection at 65°–70° C.
2. Cool to 25°–30° C. Charge and dissolve benzyl alcohol, sodium citrate, disodium edetate, PEG 4000, povidone and sodium carboxymethylcellulose.
3. Filter the solution and sterilize by autoclaving.
4. Make a slurry of the sterile Drug and pass it through a colloid mill.
5. Mix it well with solution from Step 3 and pass it through the mill.
6. Bring the suspension to the final volume/weight and fill into sterile containers.

Formulation 6

| Suppositories | | |
|---|---|---|
| A. Formula | | mg/supp |
| Drug | | 5.0 |
| Cocoa butter | | 1995.0 |
| | | 2000.0 mg |
| | | (2.0 g.) |

Procedure

1. Melt cocoa butter to about 32°–35° C.
2. Blend Drug into cocoa butter until well dispersed.
3. Pour into teflon-coated mold and congeal in refrigerator. Keep in refrigerator for an appropriate length of time.
4. Remove suppositories from mold.

| B. Formula | mg/supp |
|---|---|
| Drug | 100.0 |
| PEG 1000 | 1824.0 |
| PEG 4000 | 76.0 |
| | 2000.0 mg |

Procedure

1. Melt PEG 100 and PEG 4000 in one container to 50° C.
2. Add Drug to the mixture. Blend until well dispersed.
3. Pour into a mold and congeal in refrigerator. Keep in refrigerator for an appropriate length of time.
4. Remove suppositories from mold.

We claim:

1. A compound represented by formula:

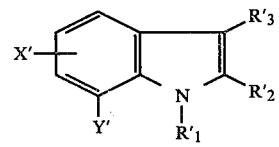

and pharmaceutically acceptable salts thereof, wherein $R'_1$ represents hydrogen or methyl;
$R'_2$ represents methyl and $R'_3$ represents methyl, cyanomethyl, or amino;
$X'$ represents hydrogen; and $Y'$ represents phenylmethoxy, 2-phenylethyl or 3-phenyl-1-propenyl.

2. A compound of claim 1 wherein $R'_1$, $R'_2$, and $R'_3$ are each methyl and $Y'$ is phenylmethoxy, i.e. 1,2,3-trimethyl-7-phenylmethoxyindole.

3. A compound of claim 1 wherein $R'_1$ is hydrogen, $R'_2$ and $R'_3$ are each methyl and $Y'$ is phenylmethoxy, i.e. 2,3-dimethyl-7-phenylmethoxyindole.

4. A compound of claim 1 wherein $R'_1$ is hydrogen, $R'_2$ is methyl, $R'_3$ is amino and $Y'$ is phenylmethoxy, i.e. 2-methyl-3-amino-7-phenylmethoxyindole.

5. A compound of claim 1 wherein $R'_1$ is hydrogen, $R'_2$ and $R'_3$ are each methyl and $Y'$ is 2-phenylethyl, i.e. 2,3-dimethyl-7-(2-phenylethyl)indole.

6. A compound of claim 1 wherein $R'_1$ is hydrogen, $R'_2$ and $R'_3$ are each methyl and $Y'$ is 3-phenyl-1-propenyl, i.e. 2,3-dimethyl-7-(3-phenyl-1-propenyl)indole.

7. A compound of claim 1 wherein $R'_1$ is hydrogen, $R'_2$ is methyl, $R'_3$ is cyanomethyl and $Y'$ is 2-phenylethyl, i.e. 2-methyl-3-cyanomethyl-7-(2-phenylethyl)indole.

8. A compound of claim 1 wherein $R'_1$ is hydrogen, $R'_2$ is methyl, $R'_3$ is amino and $Y'$ is 2-phenylethyl, i.e. 2-methyl-3-amino-7-(2-phenylethyl)indole.

9. A compound of claim 1 wherein $R'_1$ is hydrogen, $R'_2$ is methyl $R'_3$ is cyanomethyl and $Y'$ is 3-phenyl-1-propenyl, i.e. 2-methyl-3-cyanomethyl-7-(3-phenyl-1-propenyl)indole.

10. A compound of claim 1 wherein $R'_1$ is hydrogen, $R'_2$ is methyl, $R'_3$ is amino, and $Y'$ is 3-phenyl-1-propenyl, i.e. 2-methyl-3-amino-7-(3-phenyl-1-propenyl)indole.

11. A method for the treatment of the symptoms of peptic ulcer disease in mammals, which comprises administering to a mammal having peptic ulcer disease a therapeutically effective quantity of a compound of claim 1.

12. A method for the treatment of gastric ulcers in mammals which comprises administering to a mammal having gastric ulcers a therapeutically effective quantity of a compound of claim 1.

13. A method for the treatment of duodenal ulcers in mammals which comprises administering to a mammal having duodenal ulcers a therapeutically effective quantity of a compound of claim 1.

14. A method of claim 11 which comprises administering to a mammal having peptic ulcer disease, a therapeutically effecive quantity of 1,2,3-trimethyl-7-phenylmethoxyindole.

15. A pharmaceutical formulation for use in the treatment of ulcers which comprises a compound of claim 1 in a therapeutically effective amount sufficient to alleviate the symptoms of peptic ulcer disease together with a pharmaceutically acceptable carrier.

16. A pharmaceutical formulation of claim 15 which comprises a therapeutically effective amount of 1,2,3-trimethyl-7-phenylmethoxyindole together with a pharmaceutically acceptable carrier.

17. A pharmaceutical formulation of claim 15 suitable for oral administration.

18. A method of claim 11 which comprises administering to a mammal having peptic ulcer disease, a therapeutically effective quantity of 2,3-dimethyl-7-phenylmethoxyindole.

19. A method of claim 11 which comprises administering to a mammal having peptic ulcer disease, a therapeutically effective quantity of 2-methyl-3-amino-7-phenylmethoxyindole.

20. A method of claim 11 which comprises administering to a mammal having peptic ulcer disease, a therapeutically effective quantity of 2,3-dimethyl-7-(2-phenylethyl)indole.

21. A method of claim 11 which comprises administering to a mammal having peptic ulcer disease, a therapeutically effective quantity of 2,3-dimethyl-7-(3-phenyl-1-propenyl)indole.

22. A method of claim 11 which comprises administering to a mammal having peptic ulcer disease, a therapeutically effective quantity of 2-methyl-3-cyanomethyl-7-(2-phenylethyl)indole.

23. A method of claim 11 which comprises administering to a mammal having peptic ulcer disease, a therapeutically effective quantity of 2-methyl-3-amino-7-(2-phenylethyl)indole.

24. A method of claim 11 which comprises administering to a mammal having peptic ulcer disease, a therapeutically effective quantity of 2-methyl-3-cyanomethyl-7-(3-phenyl-1-propenyl)indole.

25. A method of claim 11 which comprises administering to a mammal having peptic ulcer disease, a therapeutically effective quantity of 2-methyl-3-amino-7-(3-phenyl-1-propenyl)indole.

26. A pharmaceutical formulation of claim 15 which comprises a therapeutically effective amount of 2,3-dimethyl-7-phenylmethoxyindole together with a pharmaceutically acceptable carrier.

27. A pharmaceutical formulation of claim 15 which comprises a therapeutically effective amount of 2-methyl-3-amino-7-phenylmethoxyindole together with a pharmaceutically acceptable carrier.

28. A pharmaceutical formulation of claim 15 which comprises a therapeutically effective amount of 2,3-dimethyl-7-(2-phenylethyl)-indole together with a pharmaceutically acceptable carrier.

29. A pharmaceutical formulation of claim 15 which comprises a therapeutically effective amount of 2,3-dimethyl-7-(3-phenyl-1-propenyl)indole together with a pharmaceutically acceptable carrier.

30. A pharmaceutical formulation of claim 15 which comprises a therapeutically effective amount of 2-methyl-3-cyanomethyl-7-(2-phenylethyl)indole together with a pharmaceutically acceptable carrier.

31. A pharmaceutical formulation of claim 15 which comprises a therapeutically effective amount of 2-methyl-3-amino-7-(2-phenylethyl)indole together with a pharmaceutically acceptable carrier.

32. A pharmaceutical formulation of claim 15 which comprises a therapeutically effective amount of 2-methyl-3-cyanomethyl-7-(3-phenyl-1-propenyl)indole together with a pharmaceutically acceptable carrier.

33. A pharmaceutical formulation of claim 15 which comprises a therapeutically effective amount of 2-methyl-3-amino-7-(3-phenyl-1-propenyl)indole together with a pharmaceutically acceptable carrier.

* * * * *